United States Patent
Alam et al.

(10) Patent No.: US 9,743,381 B1
(45) Date of Patent: Aug. 22, 2017

(54) SYSTEM, METHOD, AND RECORDING MEDIUM FOR DETECTING AND LEVERAGING BRAIN WAVES PRESENT IN A USER'S STATE OF FLOW TO CONTROL DIGITAL AND PHYSICAL NOTIFICATIONS

(71) Applicant: International Business Machines Corporation, Armonk, NY (US)

(72) Inventors: Nebula Alam, Essendon (AU); Jorge Andres Moros Ortiz, Carlton (AU); Shaila Pervin, Docklands (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/191,681

(22) Filed: Jun. 24, 2016

(51) Int. Cl.
*H04W 68/00* (2009.01)
*H04W 68/02* (2009.01)
*A61B 5/0482* (2006.01)

(52) U.S. Cl.
CPC ........... *H04W 68/02* (2013.01); *A61B 5/0482* (2013.01)

(58) Field of Classification Search
CPC ..... G06F 3/0488; H04W 68/005; H04W 4/16; H04W 4/027; H04W 4/046; A61B 5/1118; H04L 51/24; H04L 67/10; H04L 51/32; H04L 65/4076; G08B 21/0446; G08B 21/0461
USPC ........ 455/343, 405, 574; 713/320, 300, 321; 715/863
See application file for complete search history.

(56) References Cited

U.S. PATENT DOCUMENTS

2016/0037482 A1* 2/2016 Higgins .............. H04W 68/005 455/414.1
2016/0062590 A1* 3/2016 Karunamuni ......... G06F 3/0488 715/863

* cited by examiner

*Primary Examiner* — Phuoc H Doan
(74) *Attorney, Agent, or Firm* — Louis J. Percello, Esq.; McGinn IP Law Group, PLLC

(57) ABSTRACT

A notification control method, system, and non-transitory computer readable medium, include a state of flow detecting circuit configured to detect a state of flow of brain waves of a user from user data, a notification priority setting circuit configured to set a notification priority setting by ranking a type of a notification to be delivered to a user device according to an importance of a message associated with the notification, and a notification control circuit configured to control the notification to be output on the user device at an allowable time based on a rank of the notification priority setting being higher than a rank of the state of flow of the user.

20 Claims, 5 Drawing Sheets

SYSTEM, METHOD, AND RECORDING MEDIUM FOR DETECTING AND LEVERAGING BRAIN WAVES PRESENT IN A USER'S STATE OF FLOW TO CONTROL DIGITAL AND PHYSICAL NOTIFICATIONS

BACKGROUND

The present invention relates generally to a notification control system, and more particularly, but not by way of limitation, to a system for leveraging the detection of brain waves present in state of flow (e.g., alpha and theta), to support a user's high creative concentration state. The detection can then utilized to manage, for example, all incoming notifications to the user across multi-device so that state of flow is not interrupted, and via Internet of Things (IoT) enabled devices, part of the physical environment of the person in state of flow may change (e.g., a light on the back their chair, a sign outside of their office door, etc.) can light up, with the aim to reduce interruptions and as such supporting the state of flow.

Since the introduction of mobile phones and the advances in computers, social media, games, and demands from work, a person's attention is scattered by receiving multiple alerts, and notifications that interrupt the user's concentration at any given time. Supporting the state of flow if beneficial for creativity, autonomy, productivity, and contributes to the users satisfaction.

Conventionally, notifications are delivered to the user based on static user settings such as instantly via an alert, a sound, a vibration, etc or in bulk at a specifically set time and interval. Conventional techniques to limit interruptions consider activity by the user that is detectable by the system such as an incoming phone call or interrupting other computer speech.

That is, there is a technical problem in the conventional techniques in that the conventional techniques do not consider controlling notifications, or the IoT enabled environment based on the user entering a particular state of flow according to monitoring the user's brain waves such that the notification (e.g., digital or physical) is delivered to the user causing the user to exit a particular state of flow.

SUMMARY

In view of the technical problem in the art, the inventors have considered the technical solution to the technical problem in which the system can detect when a user enters a particular state of flow, and controls the notifications received on the user's device so that unnecessary notifications are not delivered to cause the user to exit the particular state of flow. That is, the inventors have realized that the detection of brain waves can be used to manage incoming notifications to the user across multi-devices so that a state of flow is not interrupted, and, via IoT enabled devices, part of the physical environment of the person in state of flow may change (e.g., a light on the back their chair, a sign outside of their office door, etc.) can light up, with the aim to reduce interruptions and as such supporting the state of flow.

In an exemplary embodiment, the present invention can provide a notification control system, including a state of flow detecting circuit configured to detect a state of flow of brain waves of a user from user data, a notification priority setting circuit configured to set a notification priority setting by ranking a type of a notification to be delivered to a user device according to an importance of a message associated with the notification, and a notification control circuit configured to control the notification to be output on the user device at an allowable time based on a rank of the notification priority setting being higher than a rank of the state of flow of the user.

Further, in another exemplary embodiment, the present invention can provide a notification control method, including detecting a state of flow of brain waves of a user from user data, setting a notification priority setting by ranking a type of a notification to be delivered to a user device according to an importance of a message associated with the notification, and controlling the notification to be output on the user device at an allowable time based on a rank of the notification priority setting being higher than a rank of the state of flow of the user.

Even further, in another exemplary embodiment, the present invention can provide a non-transitory computer-readable recording medium recording a notification control program, the program causing a computer to perform: detecting a state of flow of brain waves of a user from user data, setting a notification priority setting by ranking a type of a notification to be delivered to a user device according to an importance of a message associated with the notification, and controlling the notification to be output on the user device at an allowable time based on a rank of the notification priority setting being higher than a rank of the state of flow of the user.

There has thus been outlined, rather broadly, an embodiment of the invention in order that the detailed description thereof herein may be better understood, and in order that the present contribution to the art may be better appreciated. There are, of course, additional exemplary embodiments of the invention that will be described below and which will form the subject matter of the claims appended hereto.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The exemplary aspects of the invention will be better understood from the following detailed description of the exemplary embodiments of the invention with reference to the drawings.

DETAILED DESCRIPTION OF THE EXEMPLARY EMBODIMENTS

Figure 1:
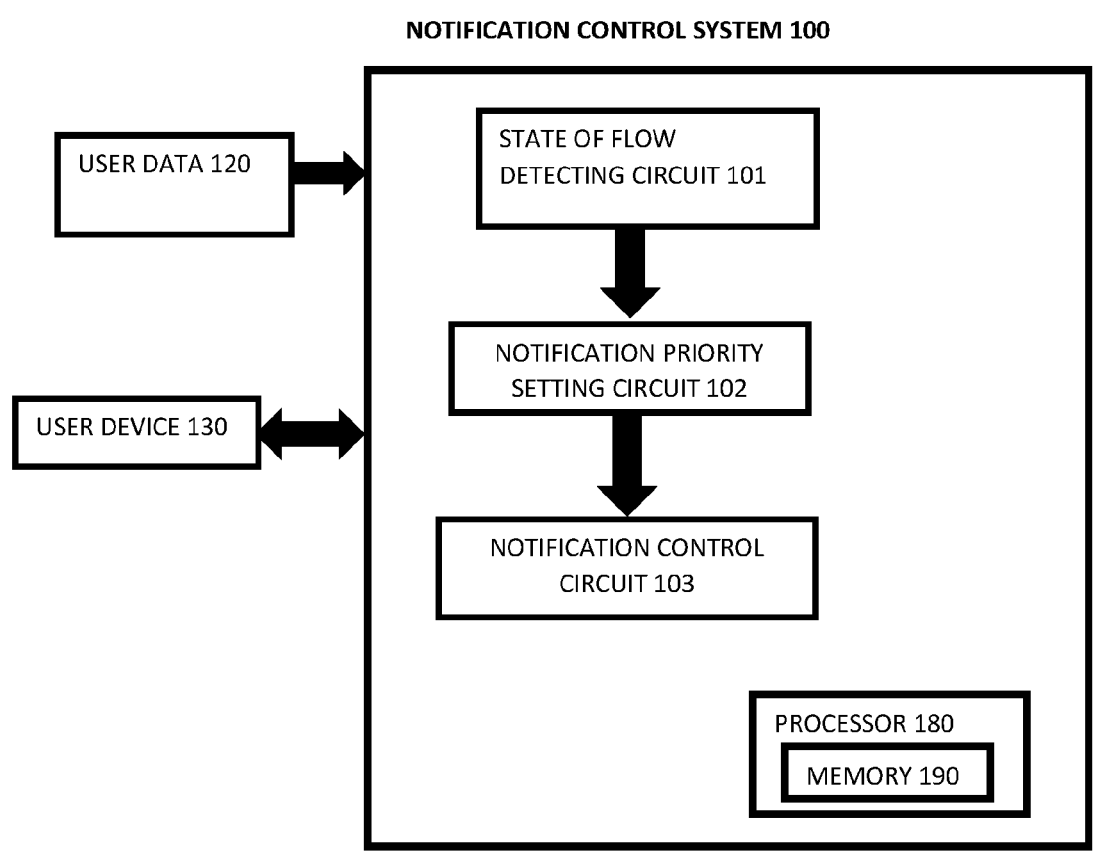
FIG. 1 exemplarily shows a block diagram illustrating a configuration of a notification control system 100.

The invention will now be described with reference to FIGS. 1-5, in which like reference numerals refer to like parts throughout. It is emphasized that, according to common practice, the various features of the drawing are not necessarily to scale. On the contrary, the dimensions of the various features can be arbitrarily expanded or reduced for clarity. Exemplary embodiments are provided below for illustration purposes and do not limit the claims.

With reference now to FIG. 1, the notification control system 100 includes a state of flow detecting circuit 101, a notification priority setting circuit 102, and a notification control circuit 103. The notification control system 100 includes a processor 180 and a memory 190, with the memory 190 storing instructions to cause the processor 180 to execute each circuit of notification control system 100. The processor and memory may be physical hardware components, or a combination of hardware and software components.

Although the notification control system 100 includes various circuits, it should be noted that a notification control system can include modules in which the memory 190 stores instructions to cause the processor 180 to execute each module of notification control system 100.

Also, each circuit can be a stand-alone device, unit, module, etc. that can be interconnected to cooperatively produce a transformation to a result.

With the use of these various circuits, the notification control system 100 may act in a more sophisticated and useful fashion, and in a cognitive manner while giving the impression of mental abilities and processes related to knowledge, attention, memory, judgment and evaluation, reasoning, and advanced computation. That is, a system is said to be "cognitive" if it possesses macro-scale properties—perception, goal-oriented behavior, learning/memory and action—that characterize systems (i.e., humans) that all agree are cognitive.

Cognitive states are defined as functions of measures of a user's total behavior collected over some period of time from at least one personal information collector (e.g., including musculoskeletal gestures, speech gestures, eye movements, internal physiological changes, measured by imaging circuits, microphones, physiological and kinematic sensors in a high dimensional measurement space, etc.) within a lower dimensional feature space. In one exemplary embodiment, certain feature extraction techniques are used for identifying certain cognitive and emotional traits. Specifically, the reduction of a set of behavioral measures over some period of time to a set of feature nodes and vectors, corresponding to the behavioral measures' representations in the lower dimensional feature space, is used to identify the emergence of a certain cognitive state(s) over that period of time. One or more exemplary embodiments use certain feature extraction techniques for identifying certain cognitive states. The relationship of one feature node to other similar nodes through edges in a graph corresponds to the temporal order of transitions from one set of measures and the feature nodes and vectors to another. Some connected subgraphs of the feature nodes are herein also defined as a "cognitive state". The present application also describes the analysis, categorization, and identification of these cognitive states further feature analysis of subgraphs, including dimensionality reduction of the subgraphs, for example graphical analysis, which extracts topological features and categorizes the resultant subgraph and its associated feature nodes and edges within a subgraph feature space.

Figure 3:
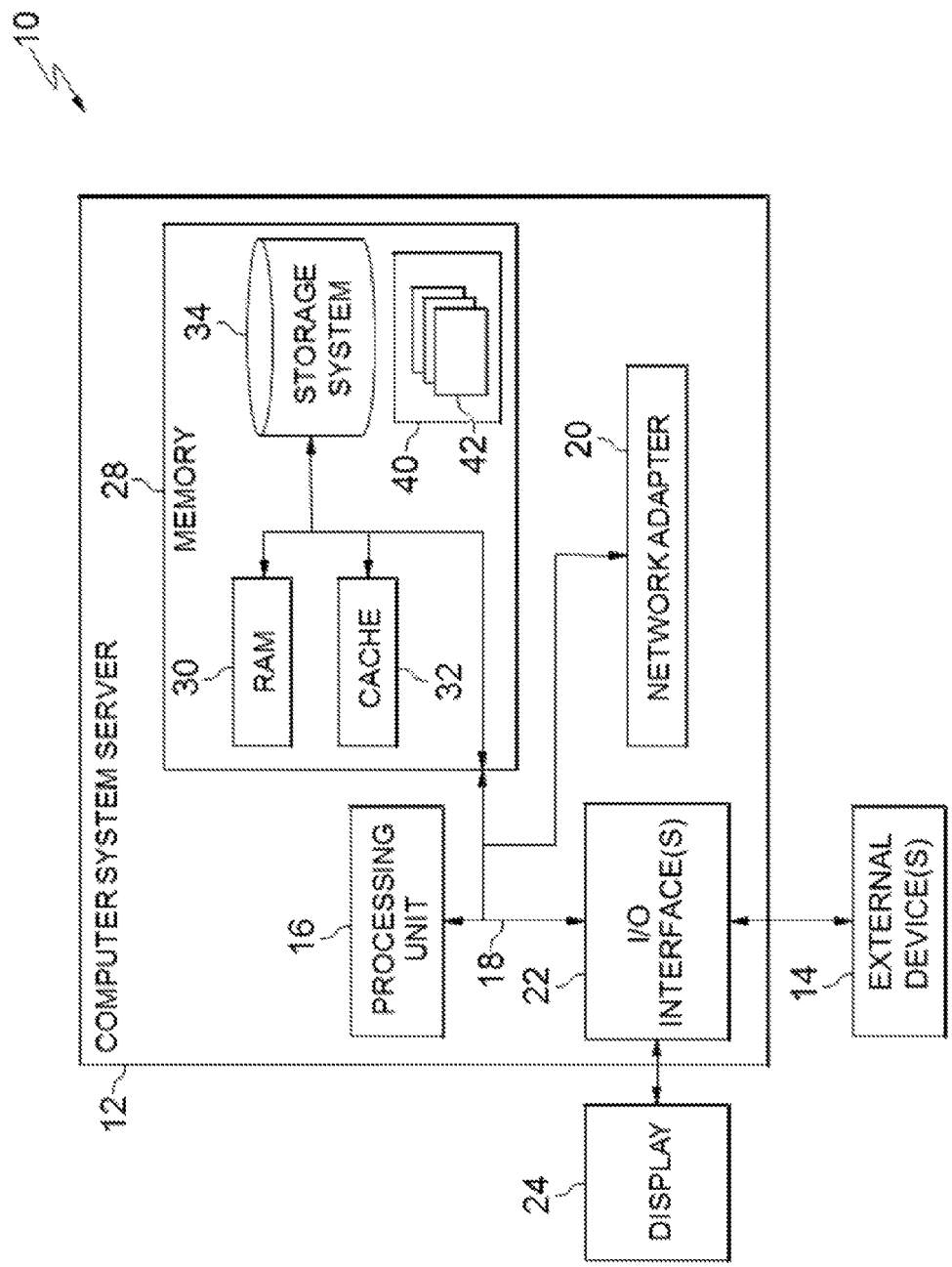
FIG. 3 depicts a cloud computing node 10 according to an exemplary embodiment of the present invention.
Figure 4:
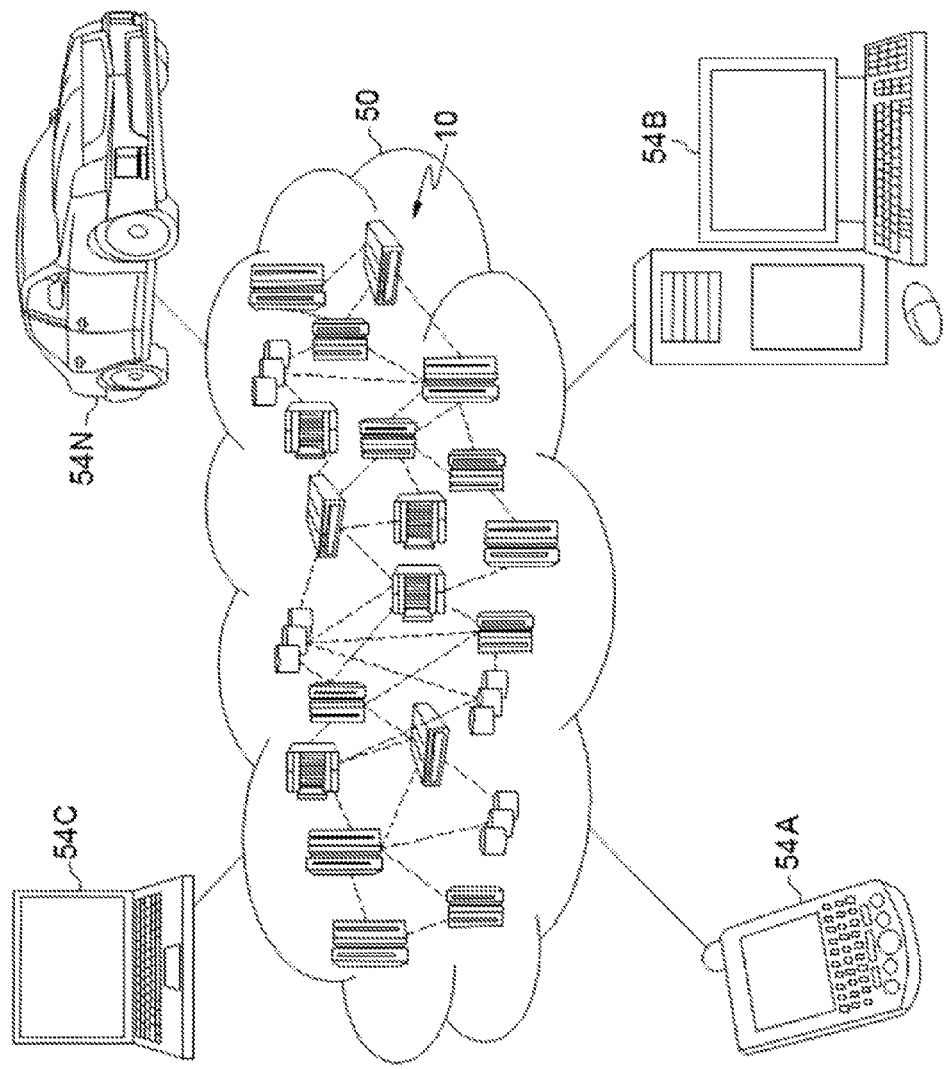
FIG. 4 depicts a cloud computing environment 50 according to another exemplary embodiment of the present invention.
Figure 5:
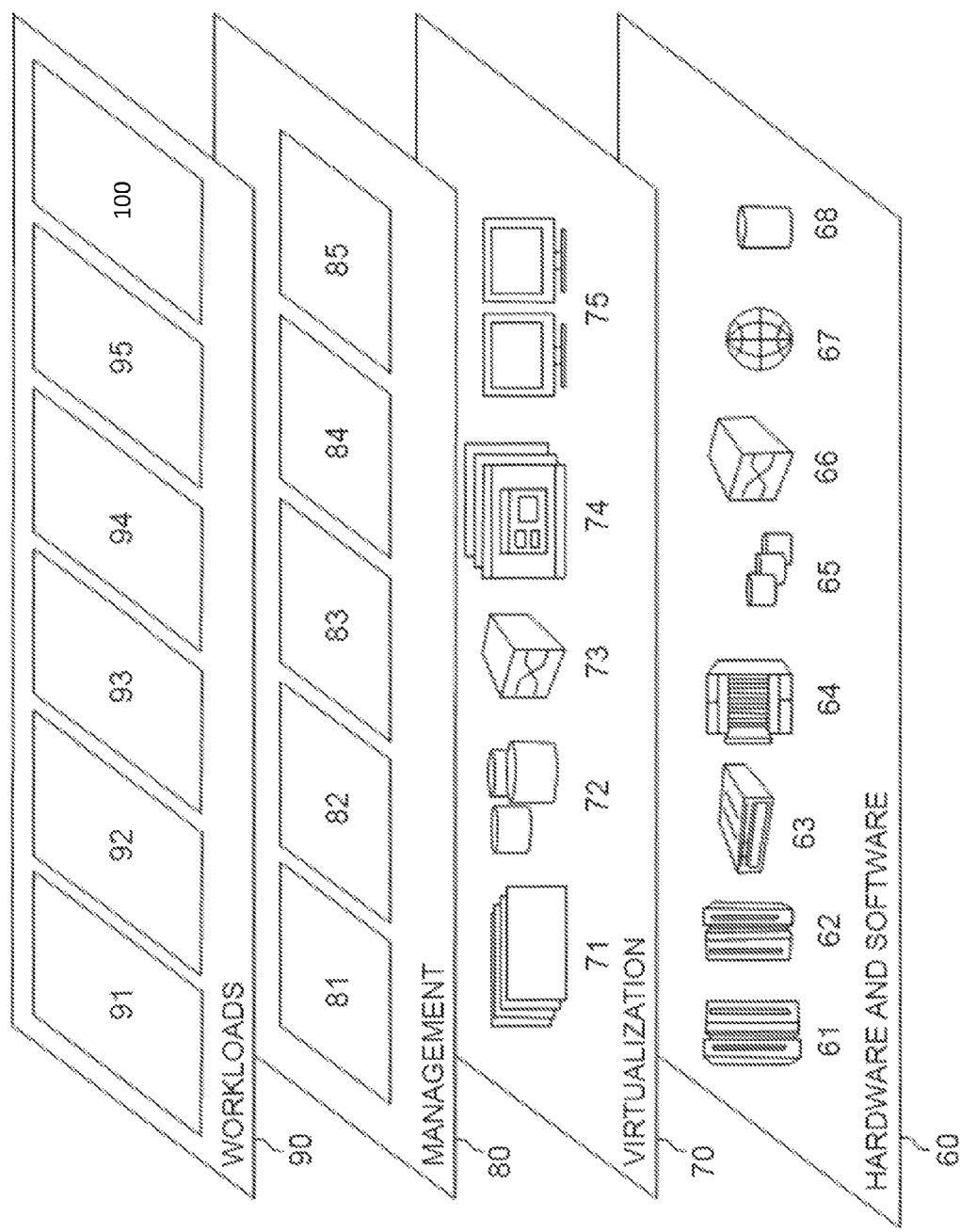
FIG. 5 depicts abstraction model layers according to an exemplary embodiment of the present invention.

Although as shown in FIGS. 3-5 and as described later, the computer system/server 12 is exemplarily shown in cloud computing node 10 as a general-purpose computing circuit which may execute in a layer the notification control system 100 (FIG. 5), it is noted that the present invention can be implemented outside of the cloud environment.

The state of flow detecting circuit 101 detects a current state of flow of the user based on user data 120. The user data 120 is based on five different types of electrical patterns or "brain waves" across the cortex in order of highest frequency to lowest (i.e., gamma, beta, alpha, theta, and delta). The brain waves can be collected (e.g., monitored) by the state of flow detecting circuit 101 with an electroencephalograph (EEG) or the like that can be obtained from user data 120 input into the system 100 from, for example, wearables, sensors, or the like. That is, the state of flow detecting circuit 101 receives brain wave data from the user data 120 from any device or system capable of monitoring brain waves of the user and detects the state of flow of the user.

Preferably, the state of flow detecting circuit 101 detects when the user has an alpha state of flow or a theta state of flow. The alpha state of flow indicates that the user is about to enter the theta state of flow. The theta state of flow is optimal for creativity, emotional connection, intuition, and relaxation such that the notification control circuit 103 does not interrupt the user to cause the user to exit the preferable state of flow as described later. However, the state of flow detecting circuit 101 detects the current state of flow of the user and the notification priority setting circuit 102 and the notification control circuit 103 can be configured to deliver the notification based on a type of detected state of flow.

The notification priority setting circuit 102 sets a notification priority for when the state of flow can be interrupted by the notification control circuit 103 by setting the notification priority for a type of notification to be sent by the user device 130. That is, the notification priority setting circuit 102 ranks the type of notification to have a higher priority (or lower priority) than the current state of flow (e.g., alpha state of flow or theta state of flow) such that the notification control circuit 103 can determine whether to deliver the notification or not.

The notification priority setting circuit 102 ranks any incoming notifications and distractions to the user device 130 and based on, for example, the strength of the relationship of the sender and user, etc. and an importance of the message, the notification priority setting circuit 102 sets the priority setting of the notification. Thereby, urgent notifications can immediately be delivered (e.g., ranked higher) to the user and less important notifications (e g, ranked lower) are not delivered until later, at an approximate time, such that the user can maintain the state of flow.

The notification priority setting circuit 102 can set the priority setting of the notification based on Natural Language Processing (NPL) of the message associated with the notification. For example, if "urgent" words or a time are associated with the message such as "emergency", "very urgent", "immediate response", "five minutes from now", etc., the notification priority setting circuit 102 can rank these types of messages as more important than a theta state of flow such that the notification is immediately delivered to the user.

The notification priority setting circuit 102 can also rank the activity of the user while in the state of flow such that the notification is weighed against the current activity of the user. For example, if the user is in a theta state of flow while casually reading articles for entertainment, the user activity is ranked lower and the priority setting of the notifications can interrupt the theta state of flow. Alternatively, if the user is working on an important project having high implications, the same notification is set to have a priority setting ranked lower than the activity of the user because the importance of the activity of the user is increased. Thus, the notification priority setting circuit 102 considers a task at hand, device interactions, what program is being used, what is the context of the user to rank the notification and set the priority of the notification, etc.

The user also can set a desired "conditional interruption" preference by inputting to the notification priority setting circuit 102 how and when, if ever, the user would like to be interrupted by a notification. Conditional interruption preferences can include, for example, a type of notification to always deliver, an activity to always (or never) interrupt, a timing of a notification (i.e., always deliver the notification if the message relates to an event within a threshold time of the notification), or identity or relationship of the sender, etc.

Further, the notification priority setting circuit 102 can "learn" from feedback of user data 120 such that the notification priority setting circuit 102 can customize the priority setting(s) for different users. For example, if the notification priority setting circuit 102 sets a message from a spouse as ranking higher than a theta state of flow but the user never checks the user device 130 (i.e., reads the message associated with the notification) when the user is interrupted and exits the theta state of flow, the notification priority setting circuit 102 can learn from this user feedback and update the priority setting of messages from the spouse to be ranked less than the theta state of flow.

The notification control circuit 103 receives the notification priority setting(s) from the notification priority setting circuit 102 and determines an allowable time to cause the user device 130 to output the notification based on the notification priority settings and the state of flow of the user.

For example, the notification control circuit 103 can determine an instantaneous generation of the notification such that the user device 130 immediately delivers the notification if the notification priority setting is "higher" than the current state of flow or the user input that the particular notification should always be delivered.

Further, the notification control circuit 103 can determine not to send the notification and instead wait for the users' state of flow or activity to be ranked less than the priority setting of the notification (i.e., user exits the state of flow by themselves) as detected/predicted by the state of flow detecting circuit 101.

Moreover, the notification control circuit 103 can cause the user device 130 to output the notification according to a periodic schedule in which the notification control circuit 103 interrupts the user regardless of the state of flow of the user at the predetermined time (e.g., once an hour, once a day, etc.). Thus, when the time in the periodic schedule occurs to deliver the notifications, the notification control circuit 103 causes the user device 130 to deliver all notifications regardless of the state of flow of the user.

Further, the notification control circuit 103 can cause a message to be sent from the user device 130 to other users in a network instructing the other users not to send any messages to the user when the user enters a particular state of flow.

Also, the notification control circuit 103 can cause a physical display alert on an Internet of Things (IoT) enabled device such as on the chair of the user (e.g., a light, sign, etc.), the door to lock people out so that they cannot enter the room such that people passing by do not ask the user questions (e.g., do not interrupt the user). Thus, the notification control circuit 103 can control the user from being interrupted by messages not only on an electronic medium but also in a physical environment. Internet of Things (IoT) enabled devices include, for example, a chair with a sensor, the sensor is connected to a network wirelessly to detect when the user gets a like on Facebook®. The sensor then vibrates, changes color, etc.

Therefore, the notification control circuit 103 controls how technology (e.g., via notifications or interruptions of a state of flow) interacts with the user as well as controls how the user interacts with technology.

That is, the notification control system 100 contributes to positive technology because entering a state of flow is not predictable at times, thereby automatically detecting the state of flow (e.g., via the state of flow detecting circuit) and adjusting technology to support the interruption of the user protects and supports tightened concentration and creativity which align with fulfilling core human needs such as autonomy and competence.

Figure 2:
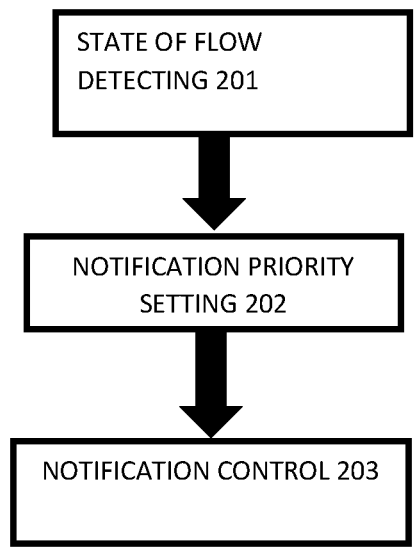
FIG. 2 exemplarily shows a high level flow chart for a notification control method 200.

FIG. 2 shows a high level flow chart for a method 200 of notification control.

Step 201 detects a state of flow of the user based on an electroencephalograph (EEG) or the like that can be obtained from user data 120.

Step 202 sets a notification priority setting by ranking any incoming notifications and distractions to the user device 130 and based on, for example, the strength of the relationship and an importance of the message, Step 202 sets the priority setting of the notification.

Step 203 controls the notifications to be output on the user device 130 at an allowable time based on the notification priority settings and the state of flow of the user.

Exemplary Hardware Aspects, Using a Cloud Computing Environment

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail) The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 3, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10, there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

As shown in FIG. 3, computer system/server 12 in cloud computing node 10 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Referring now to FIG. 4, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 5 are intended to be illustrative only and that computing nodes 10 and cloud computing environment 50 can communicate with any type of computerized circuit over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the notification control system 100 described herein.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A notification control system, comprising:
   a state of flow detecting circuit configured to detect a state of flow of a user from brain waves of the user from user data;

a notification priority setting circuit configured to set a notification priority setting by ranking a type of a notification to be delivered to a user device according to an importance of a message associated with the notification; and a notification control circuit configured to control the notification to be output on the user device at an allowable time based on a rank of the notification priority setting being higher than a rank of the state of flow of the user.

2. The system of claim 1, wherein the state of flow of the user comprises any of an alpha state of flow and a theta state of flow.

3. The system of claim 2, wherein the rank of the alpha state of flow is lower than the rank of the theta state of flow.

4. The system of claim 1, wherein the notification priority setting circuit is further configured to set the notification priority setting based on a task that the user is performing when the user has the detected state of flow.

5. The system of claim 1, wherein the notification control circuit further causes a physical notification to be displayed adjacent the user such that other users do not interrupt the state of flow of the user.

6. The system of claim 1, wherein the allowable time comprises a time when the user exits any of an alpha state of flow and a theta state of flow.

7. The system of claim 1, wherein the notification priority setting circuit sets the notification priority setting according to a user preference of a type of message to deliver the notification for while the user is in any of an alpha state of flow and a theta state of flow.

8. The system of claim 1, wherein the notification priority setting is set based on a Natural Language Processing (NLP) of the message associated with the notification.

9. The system of claim 1, wherein the user data comprises an electroencephalograph (EEG).

10. The system of claim 1, wherein the state of flow detecting circuit receives the user data from at least one of:
   a wearable; and
   a sensor.

11. The system of claim 1, wherein the importance of the message is modified by the notification priority setting circuit based on the user ignoring the message associated with the notification when the notification interrupts the state of flow of the user.

12. The system of claim 1, wherein the notification control circuit controls the notification to be output on the user device at the allowable time based on the rank of the notification priority setting being higher than the rank of the state of flow of the user such that the user maintains the state of flow if the message is ranked lower than the state of flow.

13. A notification control method, comprising:
   detecting a state of flow of a user from brain waves of a user from user data;
   setting a notification priority setting by ranking a type of a notification to be delivered to a user device according to an importance of a message associated with the notification; and
   controlling the notification to be output on the user device at an allowable time based on a rank of the notification priority setting being higher than a rank of the state of flow of the user.

14. The method of claim 13, wherein the state of flow of the user comprises any of an alpha state of flow and a theta state of flow.

15. The method of claim 14, wherein the rank of the alpha state of flow is lower than the rank of the theta state of flow.

16. The method of claim 13, wherein the setting further sets the notification priority setting based on a task that the user is performing when the user has the detected state of flow.

17. The method of claim 13, wherein the controlling further causes a physical notification to be displayed adjacent the user such that other users do not interrupt the state of flow of the user.

18. The method of claim 13, wherein the allowable time comprises a time when the user exits any of an alpha state of flow and a theta state of flow.

19. The method of claim 13, wherein the setting sets the notification priority setting according to a user preference of a type of message to deliver the notification for while the user is in any of an alpha state of flow and a theta state of flow.

20. A non-transitory computer-readable recording medium recording a notification control program, the program causing a computer to perform:
   detecting a state of flow of a user from brain waves of a user from user data;
   setting a notification priority setting by ranking a type of a notification to be delivered to a user device according to an importance of a message associated with the notification; and
   controlling the notification to be output on the user device at an allowable time based on a rank of the notification priority setting being higher than a rank of the state of flow of the user.

* * * * *